(12) United States Patent
Tran-Thi et al.

(10) Patent No.: US 9,435,746 B2
(45) Date of Patent: Sep. 6, 2016

(54) MULTIFUNCTIONAL SOL-GEL DETECTOR FOR GASEOUS COMPOUNDS AND DETECTION AND TRAPPING METHODS THEREWITH

(75) Inventors: Thu-Hoa Tran-Thi, St Fargeau-pontheirry (FR); Julien Garcia, Gif sur Yvette (FR); Thi Dinh Nguyen, Edinburgh (GB); Trung-Hieu Nguyen, Gif sur Yvette (FR)

(73) Assignees: Commissariat A L'Energie Atomique Et Aux Energies Alternatives, Paris (FR); Centre National de la Recherche Scientifique—CRNS, Paris (FR)

( * ) Notice: Subject to any disclaimer, the term of this patent is extended or adjusted under 35 U.S.C. 154(b) by 174 days.

(21) Appl. No.: 13/992,154

(22) PCT Filed: Dec. 14, 2011

(86) PCT No.: PCT/FR2011/052993
§ 371 (c)(1),
(2), (4) Date: Jun. 6, 2013

(87) PCT Pub. No.: WO2012/080665
PCT Pub. Date: Jun. 21, 2012

(65) Prior Publication Data
US 2013/0280817 A1    Oct. 24, 2013

(30) Foreign Application Priority Data
Dec. 16, 2010 (FR) ................. 10 60643

(51) Int. Cl.
*G01N 21/78* (2006.01)
*G01N 31/22* (2006.01)

(52) U.S. Cl.
CPC .......... *G01N 21/783* (2013.01); *G01N 31/224* (2013.01); *Y10T 436/173845* (2015.01); *Y10T 436/177692* (2015.01); *Y10T 436/19* (2015.01)

(58) Field of Classification Search
CPC ..................................... G01N 21/78
USPC ........ 422/82.05, 82.09, 82.11; 436/116–118, 436/124–125, 135, 111, 166, 169
See application file for complete search history.

(56) References Cited

U.S. PATENT DOCUMENTS 4,098,575 A * 7/1978 Matsushita ............. 436/20
5,292,801 A * 3/1994 Avnir ................. B01J 20/283
422/400

(Continued)

FOREIGN PATENT DOCUMENTS

JP    S63-201565 A    8/1988
JP    09-318614    * 12/1997

(Continued)

OTHER PUBLICATIONS

Anvir, D. et al, SPIE 1992, 1758, 456-463.*

(Continued)

*Primary Examiner* — Arlen Soderquist
(74) *Attorney, Agent, or Firm* — McAndrews Held and Malloy

(57) ABSTRACT

The invention relates to a multifunctional detector for gaseous compounds, or mixtures of gaseous compounds, selected from $NH_2Cl$, $NHCl_2$, $NCl_3$, total chlorine, NOx, where x=1 or 2, $O_3$, and $X_2$, where X=Cl, Br, or I, in a sample, said detector including a first sensor including an iodide and a reactive compound selected from starch, amylose, amylopectin, xyloglucan, xylan, chitosan, glycogen, polyvinyl alcohol, cellulose or a cellulose compound, α-cyclodextrin, theobromine, and polypropylene block polymers and polyethylene oxide block polymers, included in a block of sol-gel material that is absorbent in the UV spectrum but not in the visible spectrum. The invention also relates to the uses of said detector.

30 Claims, 5 Drawing Sheets

(56) References Cited

U.S. PATENT DOCUMENTS

| | | | | |
|---|---|---|---|---|
| 5,489,988 | A * | 2/1996 | Ackley | G01N 21/783 250/227.11 |
| 5,496,997 | A * | 3/1996 | Pope | G01N 21/643 250/227.21 |
| 5,637,507 | A * | 6/1997 | Wicks | C03C 1/008 422/82.06 |
| 6,022,748 | A * | 2/2000 | Charych et al. | 436/527 |
| 6,235,532 | B1 * | 5/2001 | Uttamchandani | G01N 21/7703 422/550 |
| 6,362,005 | B1 * | 3/2002 | Tanaka | G01N 21/783 422/552 |
| 7,014,816 | B2 * | 3/2006 | Miller | G01N 31/22 422/421 |
| 7,239,766 | B2 * | 7/2007 | Mechery | C03B 19/12 385/12 |
| 8,647,885 | B2 * | 2/2014 | Tran-Thi et al. | 436/165 |
| 2002/0044891 | A1 * | 4/2002 | Miller | G01N 31/22 422/421 |
| 2002/0173040 | A1 * | 11/2002 | Potyrailo | G01N 33/28 436/2 |
| 2003/0068827 | A1 * | 4/2003 | Morris | G01N 21/7703 436/136 |
| 2003/0133639 | A1 * | 7/2003 | Tao et al. | 385/12 |
| 2004/0150827 | A1 * | 8/2004 | Potyrailo | G01N 21/643 356/432 |
| 2006/0154414 | A1 * | 7/2006 | Lin | G01N 21/78 438/222 |
| 2009/0014338 | A1 * | 1/2009 | Murata | 205/777.5 |
| 2010/0075431 | A1 | 3/2010 | Zhou | |
| 2010/0136704 | A1 * | 6/2010 | Tran-Thi et al. | 436/124 |
| 2011/0319742 | A1 * | 12/2011 | Mir | A61B 5/1411 600/407 |

FOREIGN PATENT DOCUMENTS

| | | |
|---|---|---|
| JP | 2001343379 A | 12/2001 |
| JP | 2002250713 A | 9/2002 |
| JP | 2004170339 A | 6/2004 |
| JP | 2008082840 A | 4/2008 |
| JP | 2009513977 A | 4/2009 |
| WO | 2007/050463 A1 | 5/2007 |
| WO | 2010/141610 | 12/2010 |

OTHER PUBLICATIONS

Mechery, S. J. et al, Analytica Chimica Acta 2006, 557, 123-129.*
Banet, P. et al, Sensors & Transducers Journal 2007, 83, 1541-1548.*
Garcia, J. et al, 2010 First International Conference on Sensor Device Technologies and Applications 2010, 3 pages.*
Dahmouche, K. et al, Solar Energy Materials and Solar Cells 1998, 54, 1-8.*
Stathatos, E. et al, Langmuir 2000, 16, 8672-8676.*
Chaker, J. et al, Journal of Sol-Gel Science and Technology 2003, 26, 1075-1080.*
Flodstrom, K. et al, Langmuir 2004, 20, 10311-10316.*
Stathatos, E., Ionics 2005, 11, 140-145.*
Chaker, J. et al, Journal of the European Ceramic Society 2005, 25, 2617-2621.*
Portugal, I. et al, Journal of Physical Chemistry B 2010, 114, 4047-4055.*
International Search Report for International Application No. PCT/FR2011/052993, mailed May 9, 2012.
Search Report corresponding to French Patent Application No. 1060643 mailed Jul. 26, 2011.

* cited by examiner

MULTIFUNCTIONAL SOL-GEL DETECTOR FOR GASEOUS COMPOUNDS AND DETECTION AND TRAPPING METHODS THEREWITH

RELATED APPLICATIONS

The present application is filed pursuant to 35 U.S.C. §371 as a U.S. National Phase application of International Patent Application No. PCT/FR2011/052993, which was filed on Dec. 14, 2011, claiming the benefit of priority to French Patent Application No. FR 1060643 filed on Dec. 16, 2010. The entire content of each of the aforementioned applications is incorporated herein by reference in its entirety.

Chlorine is widely used for its bactericidal properties in swimming pools and in the food industry; it is employed in various chemical forms (hypochlorous acid, sodium hypochlorite or calcium hypochlorite, chlorine gas, chloroisocyanurates). It reacts with various nitrogen-containing materials in order to produce various chloramines such as monochloramine ($NH_2Cl$), dichloramine ($NHCl_2$) and trichloramine ($NCl_3$) and also organic chloramines. Given the pH of swimming pool water, the compounds that are found in the water are essentially $NH_2Cl$, $NHCl_2$ and $ClO^-$. Due to its low solubility in water, $NCl_3$ is the predominant species that is found in the atmosphere. $NCl_3$ irritates the eyes and the respiratory tracts. In particular, $NCl_3$ is a cause of chronic bronchitis problems for the monitoring staff of aquatic centres and food factories. It could also be a triggering factor for asthma, especially in children. Other byproducts such as trihalomethanes are also formed.

There is currently no regulatory value relating to air quality regarding exposure to chloramines. On the basis of the first epidemiological studies, carried out by the INRS (National Research and Safety Institute), a comfort value of 0.5 mg·m$^{-3}$ (approximately 100 ppb at 27° C.) had initially been proposed by the chemists and toxicologists of the INRS who, more recently, recommend a lower value (0.3 mg·m$^{-3}$) in a preventative approach with respect, in particular, to swimming pool monitoring staff.

The studies undertaken for quantifying the atmospheric pollution in swimming pools and in the food industry made it possible to identify an exposure of the workers to $NCl_3$ contents sometimes much higher than 0.3 mg·m$^{-3}$. They also made it possible to highlight the difficulty in being able to measure, over short durations, the contents of the various pollutants and in monitoring their variation over time, in particular for monitoring the exposure of workers in the course of one day.

There are few direct methods for assaying chloramines and even fewer methods for assaying trichloramine in the air. The known methods are either not very sensitive and non-selective, or sensitive and selective but in this case require sophisticated equipment that is complex to use.

To date, the methods commonly used for measuring chloramines are restrictive since they require a sampling step followed by a deferred laboratory analysis which is not suitable for taking a rapid decision in the event of an anomaly. Furthermore, the sampling times are at least 1 to 2 hours in order to quantify the chloramines with an acceptable accuracy, which is detrimental for demonstrating the human exposure to compounds which have short-term effects on health. Indeed, it is recommended to evaluate the maximum concentrations to which the users and operators of the establishments are exposed. From these observations, it appears that a continuous, sensitive and selective analyzer of modest cost would be of great use for the real-time monitoring of the air quality. It could, for example, be a tool of choice for the work of inspectors of regional health insurance funds. Furthermore, a continuous analyzer may prove useful for guiding the management of an establishment (e.g.: action on ventilation). Indeed, chlorine and its derivatives, despite their undesirable effects, will remain widely used in years to come since they guarantee an effective and long-lasting disinfection.

It therefore appears important to be able to have sensitive and selective instruments for continuously measuring chloramines. It would be better to also be able to detect them in solution, especially in water.

Furthermore, nitrogen dioxide ($NO_2$) forms in the atmosphere from nitrogen monoxide (NO) which is essentially released during combustion of fossil fuels, in vehicular traffic for example. Nitrogen dioxide is converted in the atmosphere into nitric acid, which falls on the ground and on vegetation. This acid contributes, in combination with other pollutants, to the acidification of natural environments.

According to the World Health Organization (WHO), nitrogen dioxide has damaging effects on health: long-term exposure may adversely affect pulmonary function and increase the risks of respiratory disorders. Nitrogen dioxide penetrates into the deep respiratory tracts where it weakens the pulmonary mucous membrane in the face of infectious attacks, especially in children. At the concentrations customarily encountered (less than about 10 ppm), nitrogen dioxide causes bronchial hyperactivity in asthmatics.

Thus, $NO_2$ is a harmful gas for various reasons:
- Effects on health: nitrogen dioxide is an irritant for bronchi. It leads to cell membrane lipid peroxidation and induces the release of powerful free radicals.
- Effects on plants: $NO_2$ participates in acid rain phenomena. The deleterious effects of nitrogen oxides on plants are the reduction in growth, the reduction in production and the resistance to pesticides.
- Effects on materials: nitrogen oxides increase corrosion phenomena.

It therefore also appears important to be able to have sensitive, rapid and inexpensive instruments for continuously measuring nitrogen oxides or else colorimetric methods that are sensitive enough for a visual detection.

Furthermore, ozone is one of the air pollutants that is dangerous to health. Beyond certain thresholds, ozone causes bronchial irritations that may be very significant in the most sensitive populations.

Ozone is highly present in and around large agglomerations where pollutants that are its precursors, in particular nitrogen dioxide $NO_2$, are produced. During heatwaves, ozone is found in large amounts in the low layers of the atmosphere, especially around urban centers. It is mainly produced therein by the reaction of unburnt hydrocarbons and nitrogen oxides from vehicle exhaust gases with oxygen from the air under the influence of sunlight. Similarly, forest fires are also an important source thereof, from the hydrocarbons and nitrogen oxides that they release. During high temperatures, the dispersion of ozone to the upper layers of the atmosphere is slowed down, optionally inducing health problems in sensitive people.

Ozone is also produced with storm lightning and also, more generally, from any spark or electric arc. Photocopiers and laser printers, high-power UV lamps or electric motors generate ozone, which may lead to significant concentrations in poorly ventilated premises.

As regards nitrogen oxides NO and ozone $O_3$, there are, in both cases, sensitive measurement methods that nevertheless require sophisticated equipment that is complex to use.

Colorimetric detection sensors have also been developed. The latter may be in the form of a dosimeter. They enable an approximate quantification of the concentration of pollutant to which the workers are exposed and have more of a warning role. When they are combined with measurement instruments (UV-visible absorption spectrometer), the quantification is accurate, sensitive (a few ppb) and rapid (a few seconds). Nevertheless, the detection is carried out in the UV range and not in the visible range.

It therefore also appears important to be able to have sensitive, rapid and inexpensive instruments for continuously measuring ozone or else colorimetric methods that are sensitive enough to enable a visual detection.

It would therefore be particularly desirable to have a sensitive, rapid and inexpensive device for continuously measuring all or some of the aforementioned compounds or else colorimetric methods that are sensitive enough for the visual detection thereof.

Garcia, J. et al. describe in "Chemical sensors for the detection of chlorine and nitrogen trichloride at ppb level", Proceedings—1st International Conference On Sensor Device Technologies And Applications, Sensordevices 2010—Proceedings—IEEE COMPUTER SOCIETY U, July 2010 (2010-07), a process for detecting toxic gases using a thin film of nanoporous and nanostructured silicate, doped with a brominated surfactant compound, decamethonium bromide.

But the tribromide does not form stable complexes, which absorb in the visible, with the polymers (amylose, polyvinyl alcohol, etc.). Moreover, the surfactants are used for organizing a crown of Br ions in the pores as explained by C. J. Brinker, Y. Lu, A. Sellinger, H. Fan, "Evaporation-induced self-assembly: nanostructures made-easy", Adv. Mat., 11(7), 579-585, (1999) or M. F. Cardinal, M. Lovino, D L. Bernik, "Comparative study of the porosity induced CTAB and tween as silica templates", Mat. Sci. Eng. C27, 75-79, (2007).

After lengthy research, the applicants have developed satisfactory devices.

This is why one subject of the present application is a multifunctional detector for gaseous compounds or mixtures of gaseous compounds using a novel type of sensor. The gaseous compounds or mixtures of gaseous compounds may be in the form of gas or in solution, in particular aqueous solution.

The novel type of sensor comprises two essential elements:
  an iodide and
  a reactive compound selected from starch, amylose, amylopectin, xyloglucan, xylane, chitosan, glycogen, polyvinyl alcohol or a polyvinyl alcohol compound, cellulose or a cellulose compound, α-cyclodextrin, theobromine and block polymers of polypropylene oxides and polyethylene oxides. In the invention, these compounds are used for trapping and forming colored complexes with $I_3^-$ and $I_2$.

The above compound is preferably selected from starch, amylose, amylopectin, xyloglucan, xylane, chitosan, glycogen, polyvinyl alcohol or a polyvinyl alcohol compound, cellulose or a cellulose compound, α-cyclodextrin and theobromine.

The polyvinyl alcohol compounds are esters such as polyvinyl acetate, or other types of derivatives such as polyvinyl pyrrolidone. The cellulose compounds are, for example, cellulose ethers such as carboxymethyl cellulose and cellulose esters that are more soluble in water than cellulose. A block polymer of polyethylene oxides and polypropylene oxides is in particular the triblock polymer used in the synthesis of SBA-15 mesoporous silicas, sold under the name Pluronic® P123.

According to the invention, the sensor is bifunctional. When the sample to be tested is gaseous, a portion of a native gas mixture to be studied may come into direct contact with a sensor comprising an iodide and a reactive compound selected from starch, amylose, amylopectin, xyloglucan, xylane, chitosan, glycogen, polyvinyl alcohol or a polyvinyl alcohol compound, cellulose or a cellulose compound, α-cyclodextrin, theobromine and block polymers of propylene oxides and polyethylene oxides, and another portion of the gas mixture to be studied may come into contact with such a sensor, but after treatment with a filter comprising a neutral silicate matrix impregnated with sulfamic acid. When the sample to be tested is liquid, the liquid sample is brought into contact with such a sensor. The term "neutral" means that the matrix does not contain probe molecules.

This is why one subject of the present application is a multifunctional detector for gaseous compounds or mixtures of gaseous compounds selected from $NH_2Cl$, $NHCl_2$, $NCl_3$, total chlorine, $NO_x$ where x=1 or 2, $O_3$ and $X_2$ where X=Cl, Br or I in a sample, comprising a first sensor comprising an iodide and a reactive compound selected from starch, amylose, amylopectin, xyloglucan, xylane, chitosan, glycogen, polyvinyl alcohol or a polyvinyl alcohol compound, cellulose or a cellulose compound, α-cyclodextrin, theobromine and block polymers of polypropylene oxides and polyethylene oxides, incorporated into a block of sol-gel material that absorbs in the UV but not in the visible.

The above polymers form stable complexes which absorb in the visible with the triiodide. It should be noted that the named polymers are not surfactants, nor used as such. Their role is to form triiodide complexes.

The total chlorine corresponds to the sum of the combined chlorine ($NH_2Cl+NHCl_2+NCl_3$) and of the free chlorine ($Cl_2$ or ClOH or $ClO^-$). In what follows, the expression "gaseous compound" will also apply to a mixture of gaseous compounds, except when the context indicates the contrary.

Under preferred conditions for implementing the invention, the above multifunctional detector is suitable for gaseous compounds or mixtures of gaseous compounds selected from $NH_2Cl$, $NHCl_2$, $NCl_3$, total chlorine, $NO_x$ where x=1 or 2, $O_3$ and $X_2$ where X=Cl, Br or I, in a sample in gas form and further contains:
  a filter comprising a neutral silicate matrix impregnated with sulfamic acid,
  means for bringing a first portion of the gas mixture directly into contact with the first sensor,
  means for bringing a second portion of the gas mixture into contact with the first sensor, after having passed through the filter.

Under other preferred conditions for implementing the invention, the above multifunctional detector is suitable for gaseous compounds or mixtures of gaseous compounds selected from $NH_2Cl$, $NHCl_2$, $NCl_3$, total chlorine, $NO_x$ where x=1 or 2, $O_3$ and $X_2$ where X=Cl, Br or I, in a sample in gas form and also contains a second type of sensor comprising phenol incorporated into a sol-gel matrix that absorbs in the UV but not in the visible. This second sensor is used to detect only $NH_2Cl$.

This is why another subject of the present application is a multifunctional detector for gaseous compounds or mixtures of gaseous compounds selected from $NH_2Cl$, $NHCl_2$, $NCl_3$, total chlorine, $NO_x$ where x=1 or 2, $O_3$ and $X_2$ where X=Cl, Br or I, in a sample in gas form comprising:

- a first sensor comprising an iodide and a reactive compound selected from starch, amylose, amylopectin, xyloglucan, xylane, chitosan, glycogen, polyvinyl alcohol or a polyvinyl alcohol compound, cellulose or a cellulose compound, α-cyclodextrin, theobromine and block polymers of polypropylene oxides and polyethylene oxides, incorporated into a block of sol-gel material that absorbs in the UV but not in the visible, and
- a second sensor comprising phenol and sodium nitroprussiate incorporated into a block of sol-gel material that absorbs in the UV but not in the visible,
- a filter comprising a neutral silicate matrix impregnated with sulfamic acid,
- means for bringing a first portion of the gas mixture directly into contact with the first sensor,
- means for bringing a second portion of the gas mixture into contact with the first sensor, after having passed through the filter,
- means for bringing a third portion of the gas mixture directly into contact with the second sensor.

In the present application and in what follows, the term "matrix" denotes the sol-gel material doped with reactant(s) and in particular probe molecules. The expression "desired gaseous compound" denotes the desired gaseous compound(s) in the sample, for example the gas mixture, tested. The compounds of the first sensor or of the second sensor incorporated into a block of sol-gel material will be generically referred to as the "probe molecules".

As a reminder, a sol-gel material is a material obtained by a sol-gel process that consists in using, as precursors, alkoxides of formula $M(OR)_n$ where M is a metal, in particular silicon, and R is an alkyl group, and in hydrolyzing them. In the presence of water, the hydrolysis of the alkoxy (OR) groups takes place, forming small particles having a size generally of less than 1 nanometer. These particles aggregate and form clusters which remain in suspension without precipitating, and form a sol. The increase in the clusters increases the viscosity of the medium which gels. A sol-gel material is obtained by drying of the gel, by evacuating the solvent out of the polymeric network formed.

The probe molecules are incorporated into a block of sol-gel material that absorbs in the UV but not in the visible. One of the probe molecules is an iodide, which may be sodium iodide, potassium iodide or else ammonium iodide. The second probe molecule is preferably amylose, preferably comprising from 40 to 3000 glucose units and especially from 250 to 350 glucose units, particularly 300 glucose units.

The block polymers of polypropylene oxides and polyethylene oxides are, for example, Pluronic® P123 having a number-average molecular weight preferably from 1500 to 4000, especially 2800.

The polyvinyl alcohol compounds are, for example, polyvinyl acetates having a molecular weight preferably from 60 000 to 200 000, especially 80 000, or polyvinyl pyrrolidones having a molecular weight preferably from 8000 to 40 000, especially 15 000. The polyvinyl alcohol has a molecular weight preferably of greater than 60 000 and especially 125 000.

The preferred reactive compound are advantageously chosen as above.

One or more of the gaseous compounds or mixtures of gaseous compounds $NH_2Cl$, $NHCl_2$, $NCl_3$, total chlorine, $NO_x$ where x=1 or 2, $O_3$ and $X_2$ where X=Cl, Br or I may be present in a gas mixture. They may in particular be present in a gas such as those that are encountered in particular in the production or research departments of various industries or activities such as those mentioned previously, and particularly in the semiconductor industry.

In the atmosphere, $NCl_3$, $NHCl_2$, $NH_2Cl$ and sometimes $Cl_2$ in a small amount will thus be found. In swimming pool water, which has a pH from 6.5 to 7.5, $ClO^-$, $NCl_3$, $NHCl_2$, $NH_2Cl$ and ClOH are found.

In a block of sol-gel material of the first sensor, the iodide advantageously represents from 0.0054% to 0.55%, preferably from 0.01% to 0.11%, in particular around 0.055% by weight of the block. The other probe molecule advantageously represents from 0.05% to 0.25%, preferably from 0.1% to 0.2%, in particular around 0.17% by weight of the block. The remainder of the block is essentially (more than 90%, in particular more than 95%, particularly more than 99%) or completely constituted of the sol-gel material.

In a block of sol-gel material of the second sensor, the phenol advantageously represents from 10% to 25%, preferably from 11% to 18%, in particular around 14% by weight of the block. Sodium nitroprussiate advantageously represents from 0.01% to 0.25%, preferably from 0.03% to 0.11%, in particular around 0.06% by weight of the block. Finally, the sodium hydroxide advantageously represents from 1% to 17%, preferably from 3% to 12% and in particular around 6% by weight of the block. The remainder of the block is essentially (more than 90%, in particular more than 95%, particularly more than 99%) or completely constituted of the sol-gel material.

In a filter comprising a neutral silicate matrix, the sulfamic acid advantageously represents from 5% to 15%, preferably from 8% to 12%, in particular around 10% by weight of the matrix block, that is to say of the weight of all of the silicate and sulfamic acid constituents of the neutral silicate matrix.

Under preferred conditions for implementing the invention, the sensors are initially transparent.

A first sensor may be prepared as follows:
- a reactive compound selected from starch, amylose, amylopectin, xyloglucan, xylane, chitosan, glycogen, polyvinyl alcohol or a polyvinyl alcohol compound, cellulose or a cellulose compound, α-cyclodextrin, theobromine and block polymers of polypropylene oxides and polyethylene oxides is dissolved in an aqueous solution,
- the mixture is homogenized, for example in an ultrasound bath, then brought to boiling and subsequently cooled to ambient temperature,
- an alkoxide of formula $M(OR)_n$ where M is a metal, in particular silicon, and R is an alkyl group, for example tetramethoxysilane, is added, then sodium iodide in solid form is added,
- the sol is stirred in the dark and at ambient temperature for 10 to 20 minutes and in particular around 12 minutes,
- the sol is withdrawn in order to pour it into molds which are hermetically sealed for 24 hours then the caps are replaced by a porous film,
- it is then kept in the dark in order to obtain a block of sol-gel material containing the desired probe molecules.

A second sensor may be prepared, for example, as follows:

phenol, sodium nitroprussiate and sodium hydroxide are dissolved in a mixture of Millipore water and methanol, the solution is stirred, then immersed in a bath of ethanol cooled to minus (−) 18° C., an alkoxide of formula $M(OR)_n$ where M is a metal, in particular silicon, and R is an alkyl group, for example tetramethoxysilane, is added, the solution is kept at −18° C., with stirring, for 1 minute; the molar ratio of the final mixture of the precursors is tetramethoxysilane/methanol/water 1/2/6, the sol is withdrawn in order to pour it into molds which are hermetically sealed, it is then kept in the dark for 20 days in order to obtain a block of sol-gel material containing the desired probe molecules.

A multifunctional detector of the invention may take several forms depending on whether it is intended for a gaseous or liquid sample.

When intended for a gaseous sample, it may take the form of a compartmentalized support, a first compartment containing a first sensor and another compartment containing a second sensor. In particular, it may take the form of a compartmentalized support, a first compartment containing a first sensor and another compartment containing a second sensor, the first compartment preferably itself being compartmentalized in order to divide the flow into two, one portion of the flow passing through a filter above before reaching the first sensor.

When intended for a liquid sample, it may take the form of a disk of fixed thickness, placed in a multi-well plate; it may especially take the form of a thin layer, for example fastened to a strip of plastic to be dipped into the liquid sample. The thin layer may comprise a cellulose support, for example filter paper, impregnated with probe molecules.

The multifunctional detectors that are the subject of the present invention have very advantageous properties and qualities. In particular, a color change of a first sensor, of the second sensor or of the various sensors occurs in contact with the desired gaseous compounds contained in a studied gas mixture, or a color change of a first sensor or a second sensor or of both sensors occurs in contact with desired gaseous compounds contained in a studied liquid sample.

The reactions that take place at a first sensor between the reactive compounds and a desired gaseous compound ($NCl_3$, total chlorine, $NO_x$ where x=1 or 2, or else $O_3$, $X_2$ where X=Cl, Br or I) give rise to the formation of a product, the absorbent properties of which are different from those of the initial reactive compounds. The reactants are inserted into a polymer (sol-gel) matrix in order to give a hybrid organic-inorganic compound and absorb in the UV but not in the visible. The products of the reaction between the various reactive compounds and the desired gaseous compounds absorb in the visible. The optical detection is rapid and can be carried out in situ in a single step. In order to detect a coloration, the light sources that can be used in the visible, such as light-emitting diodes, make it possible to reduce the cost of the optical equipment.

The formation of a complex between the reactive compound of the first sensor and $I_3^-$ ions produces a coloration in the visible. For example, the formation of an amylose/$I_3^-$ complex absorbs at 580 nm. Depending on the nature of the reactive compound, the complex formed absorbs in the visible with a position of the absorption maximum located from 460 to 680 nm.

The formation of a complex between the reactive compound of a first sensor and the trichloramine also produces a coloration in the visible.

In this case, the gas mixture tested is first treated in order to eliminate all the chlorinated species with the exception of the trichloramine $NCl_3$. For this purpose, the gas mixture passes through a filter consisting of a neutral silicate matrix impregnated with sulfamic acid, in which medium only the trichloramine is insoluble and stable. If a gas mixture now containing only trichloramine is brought into contact with the first sensor, the formation of a complex between the reactant of the first sensor and $I_3^-$ ions formed, produces a coloration in the visible, for example again the formation of an amylose/$I_3^-$ complex that absorbs at 580 nm.

Thus, the first sensor is by itself bifunctional, since it acts in part with a flow of native gas mixture and in part with a flow of pretreated gas.

The reaction that takes place at the second sensor between the phenol and the monochloramine $NH_2Cl$ gives rise to the formation of a product, the absorbent properties of which are different from those of the initial reactive compounds. The phenol is inserted with sodium nitroprussiate, catalyst of the reaction, into a polymer matrix in order to give a hybrid organic-inorganic compound and absorbs in the UV but not in the visible. The product of the reaction between the phenol and the monochloramine, an indophenol derivative, absorbs in the visible at 635 nm.

This is why another subject of the present application is a process for detecting gaseous compounds or mixtures of gaseous compounds selected from $NH_2Cl$, $NHCl_2$, $NCl_3$, total chlorine, NO where x=1 or 2, $O_3$ and $X_2$ where X=Cl, Br or I, contained in a liquid or gaseous sample, characterized in that a multifunctional detector above comprising a first sensor is brought into contact with the sample and in that the optional color change of the blocks of sol-gel material constituting the first sensor is observed.

Another subject of the present application is a process for detecting gaseous compounds selected from $NH_2Cl$, $NHCl_2$, $NCl_3$, total chlorine, $NO_x$ where x=1 or 2, $O_3$ and $X_2$ where X=Cl, Br or I, contained in a gas mixture, characterized in that a multifunctional detector above comprising a first sensor and a second sensor is exposed to a flow of a gas mixture and in that the optional colour change of the blocks of sol-gel material constituting the first sensor or the second sensor is observed.

The gas flow capable of containing gaseous compounds to be detected or studied may originate from a polluted atmosphere. It may in particular circulate at a flow rate of 10 $mL \cdot min^{-1}$ to 1.1 $L \cdot min^{-1}$.

Under other preferred conditions for implementing the invention, a first portion of the gas mixture is brought directly into contact with a first block of a first sensor, and a second portion of the gas mixture is brought into contact, after having passed through the filter, with a second block of a first sensor. In other words, use is made of two distinct blocks of the first sensor depending on whether the gas mixture arrives directly or after having passed through the filter above.

In the case of a liquid sample, an amount of liquid (for example a drop or a microdrop) is placed on a block of sol-gel material constituting the first sensor or the second sensor, or on a block of sol-gel material constituting the first sensor and a block of sol-gel material constituting the second sensor.

Depending on the amount of reactive compounds, it is possible, in addition to the detection of gaseous compounds, to carry out the trapping thereof.

This is why another subject of the present application is a process for trapping gaseous compounds selected from $NH_2Cl$, $NHCl_2$, $NCl_3$, total chlorine, $NO$ where x=1 or 2, $O_3$ and $X_2$ where X=Cl, Br or I, contained in a gas mixture, characterized in that a multifunctional detector above comprising a first sensor and a second sensor is exposed to a flow of a gas mixture in order to obtain a gas mixture without any gaseous compound selected from $NH_2Cl$, $NHCl_2$, $NCl_3$, total chlorine, $NO$ where x=1 or 2, $O_3$ and $X_2$ where X=Cl, Br or I, or a gas mixture with a lower content of such gaseous compounds.

Monitoring the coloration as a function of time makes it possible to determine the rate of the reaction, which is proportional to the concentration of desired gaseous compound.

This is why another subject of the present application is a process for evaluating the amount or concentration of gaseous compounds above contained in a gas mixture, characterized in that the coloration is monitored as a function of time. From this monitoring, it is possible to deduce the aforementioned evaluation.

Monitoring the coloration as a function of time can be carried out, for example, by absorption spectroscopy. A suitable device comprises at least one light excitation source and a collector.

The colour variation may especially be evaluated visually or measured accurately using an instrument based on the absorbance or reflectance.

Another subject of the present application is a system for trapping or detecting gaseous compounds using, as sensor, a multifunctional detector above comprising a first sensor or a first sensor and a second sensor.

Such a system may in particular comprise a suction device in order to give rise to a flow of a gas mixture, particularly at constant flow rate or pulsed flow rate (series of on and off phases of the flow rate), over continuous or sequential periods. It also comprises, in particular, one or more points for capturing the gas mixture, for example at a distance from the system.

It should be noted that in the present application, conventionally the indefinite article "a" should be considered as a generic plural (meaning "at least one" or else "one or more"), except when the context indicates the contrary (1 or "only one"). Thus, for example, when it is said above that the first sensor comprises an iodide salt and a reactive compound, these are one or more iodide salts and one or more reactive compounds.

The preferred implementation conditions of the multifunctional detectors described above also apply to the other subjects of the invention targeted above, in particular to the processes implementing them.

The following examples illustrate the present application.

The invention will be better understood if reference is made to the appended drawings, in which.

Figure 7:
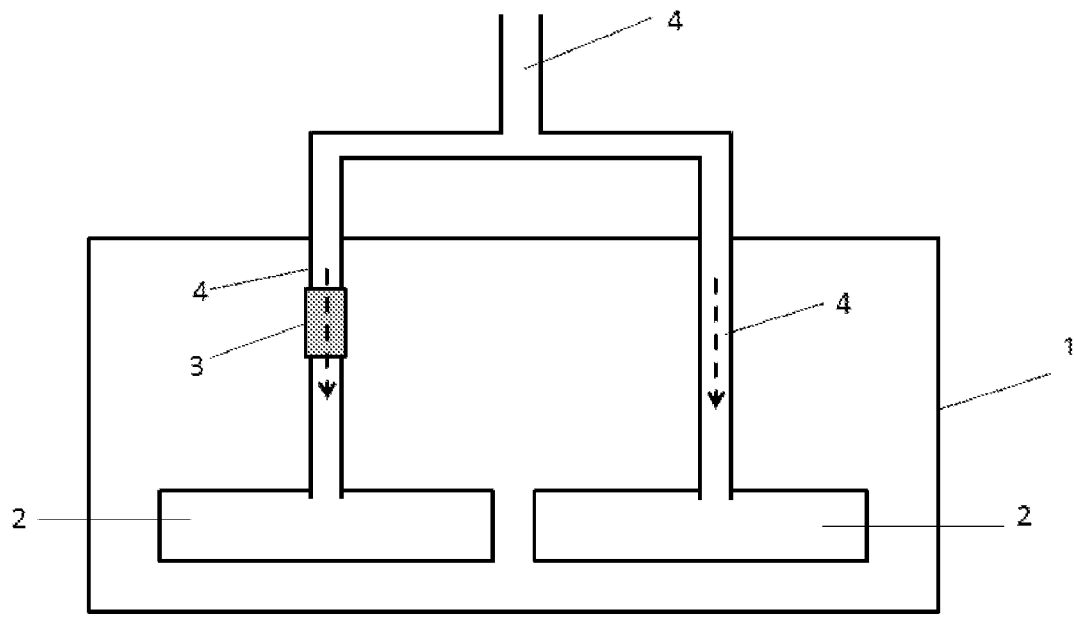

FIG. 7 is a schematic view of a multifunctional detector (1) according to one embodiment disclosed herein, including a pair of first sensors (2), a filter (3), and a compartmentalized (divided) gaseous compound or mixture flowpaths (4), where the filter (3) is in fluid connection with one of the flowpaths. The dotted arrows indicate direction of the sample flowpath, which contact the first sensors.

Figure 8:
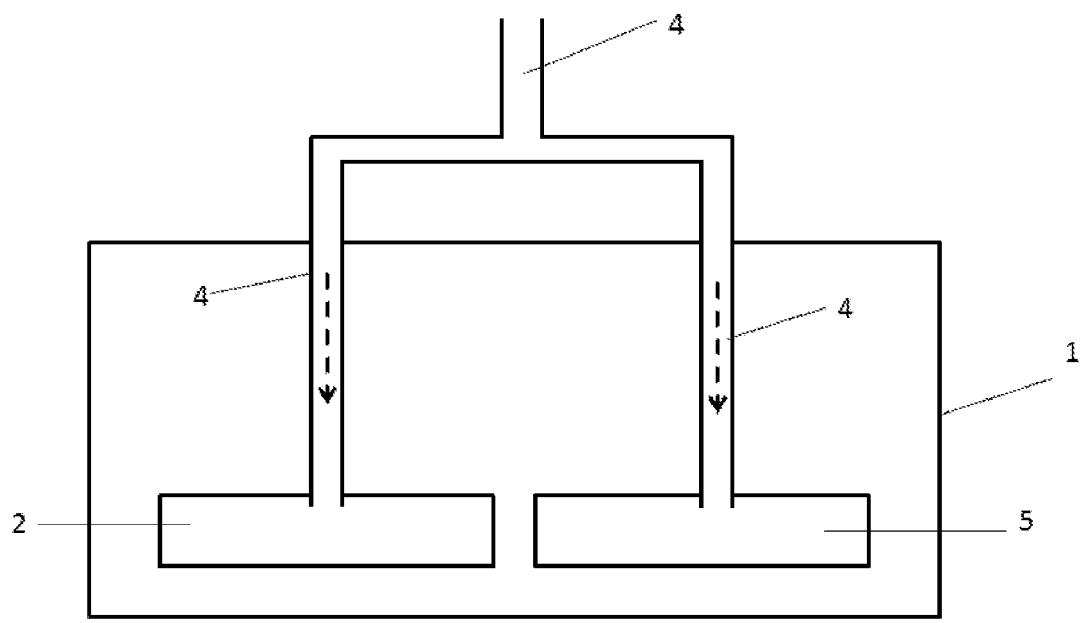

FIG. 8 is a schematic view of a multifunctional detector (1) according one embodiment disclosed herein, including a first sensor (2), a compartmentalized (divided) gaseous compound or mixture flowpaths (4), and a second detector (5).

Figure 9:
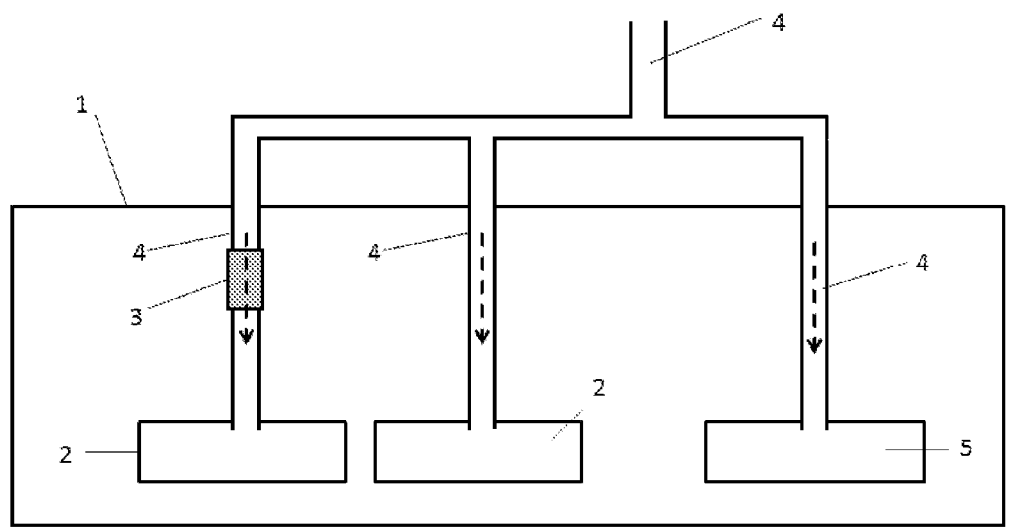

FIG. 9 is a schematic view of a multifunctional detector (1) according one embodiment disclosed herein, including a pair of first sensors (2), a filter (3), a compartmentalized (divided) gaseous compound or mixture flowpaths (4), and a second detector (5), where the filter (3) is in fluid connection with one of the two flowpaths which contact the first sensors. The dotted arrows indicate direction of the flowpaths.

EXAMPLE 1

Preparation of a First Sensor

A first sensor was produced as follows:

30 mg of amylose are dissolved in 50 ml of buffer solution at pH=4.65. The solution is introduced into an ultrasound bath for 60 minutes, then brought to boiling for 60 minutes, and finally cooled to ambient temperature.

12 ml of this amylose solution are then added to 6 ml of tetramethoxysilane. Finally, 2.7 mg of sodium iodide are added in solid form so as to obtain a concentration of $10^{-3}$ M in the final solution.

The sol is then stirred in the dark and at ambient temperature for 12 minutes. The latter is then withdrawn milliliter by milliliter and is poured back into polystyrene tanks. The latter are then hermetically sealed using a cap for 24 hours.

The next day, the caps are replaced by a porous film. The sol is then kept in the dark in order to obtain blocks of sol-gel material containing the reactant. These blocks are xerogels constituting a first sensor.

EXAMPLE 2

Preparation of a First Sensor

With the water-soluble reactive compounds, the matrices obtained by synthesis by the sol-gel process are transparent. When the reactive compound is insoluble in water, such as cellulose, blocks containing NaI or KI or $NH_4I$ may be produced from solid powder. Translucent blocks are then obtained which, exposed to chloramines, or to $NO_2$, $O_3$, $I_2$, etc., become a blue-violet color. The color is visible to the naked eye (see FIG. 5). The color variation may, if desired, be measured accurately by reflectance.

EXAMPLE 3

Preparation of a Second Sensor 47.7 mg of phenol, 20.3 mg of sodium hydroxide and also 0.2 mg of sodium nitroprussiate are taken up in 1621 µl of water and 1217 µl of methanol. The solution is then stirred and immersed in a bath of ethanol at −18° C. 2232 µl of tetramethoxysilane are then added. The solution is kept at −18° C., with stirring, for one minute. The sol is then withdrawn milliliter by milliliter and is poured back into polystyrene tanks. The latter are then hermetically sealed using a cap for 20 days.

The molar ratio of the mixture of precursors and solvents $TMOS/methanol/H_2O$ is 1/2/6.

EXAMPLE 4

Preparation of a Filter for the First Sensor

Firstly, neutral matrices are prepared in the following proportions: tetramethoxysilane/methyltrimethoxysilane/water/methanol: 0.9/0.1/4/4. In a sample tube, 3.5 ml of tetramethoxysilane, 1.88 ml of Millipore water, 4.24 ml of methanol and finally 373 µl of methyltrimethoxysilane are introduced. The solution in stirred for 30 min at ambient temperature. The sol is then withdrawn milliliter by milliliter and is poured back into plastic tanks. The latter are then hermetically sealed using a cap for 24 hours. The next day, the caps are replaced by a porous film. The sol is then kept in the dark in order to obtain blocks of sol-gel material.

7 g of blocks thus obtained (0.2 g/block) are then coarsely ground using a mortar and are impregnated with 2 ml of a saturated aqueous solution of sulfamic acid.

Experiment 1

Relationship Between the Intensity of the Colored Peak and the Amount of Product Tested A block of sol-gel material from example 1 is exposed to a continuous gas flow of 200 ml/min containing a fixed concentration of $NCl_3$ of 32 ppb. Monitoring by UV-visible absorption spectroscopy over the exposure time makes it possible to observe the appearance of a peak at 580 nm characteristic of the amylose/$I_3^-$ complex. The intensity of this peak increases in the course of the exposure, which means that the greater the amount of $NCl_3$, the greater the amount of product formed.

Figure 3:
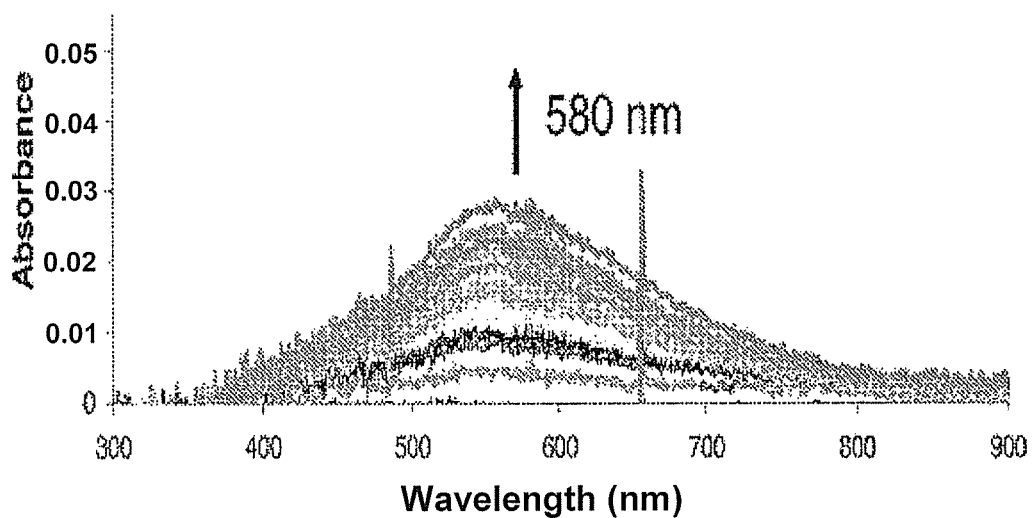
FIG. 3 represents the monitoring, by UV-visible absorption spectroscopy, of the formation of the amylose/$I_3^-$ complex over time, during the exposure of blocks of sol-gel material from example 1 to a gaseous mixture containing 32 ppb of $NCl_3$.

The results are given in FIG. 3.

Experiment 2

Application in the Detection of $NO_2$

Blocks of sol-gel material from example 1 are exposed to continuous 200 ml/min flows of nitrogen containing 10 ppm of $NO_2$. Monitoring by UV-visible absorption spectroscopy demonstrates the formation of the amylose/$I_3^-$ complex that absorbs at 580 nm.

The variation of the absorbance at 580 nm is then given as a function of the exposure time.

Figure 1:
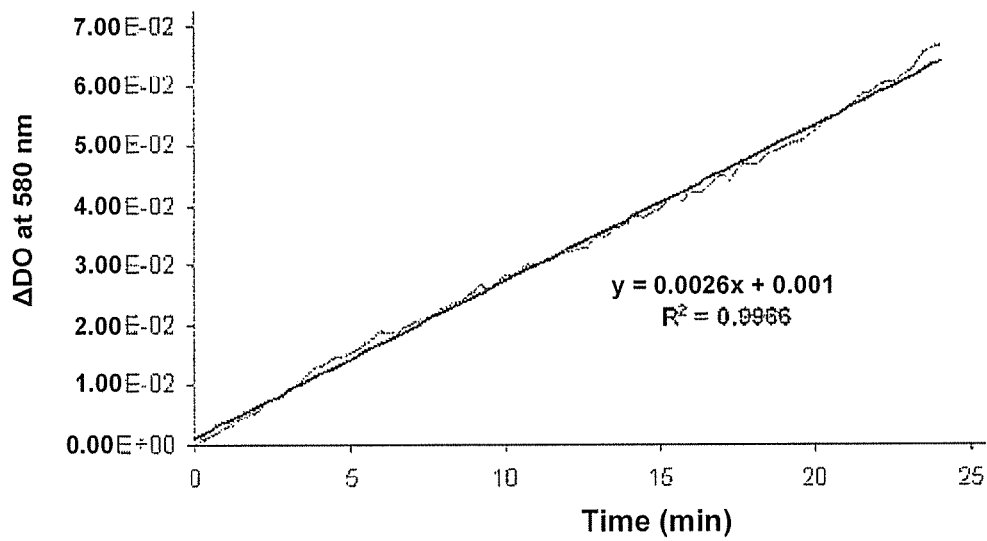
FIG. 1 represents the variation of the absorbance at 580 nm as a function of the exposure time, evaluated by UV-visible absorption spectroscopy, of a matrix of sol-gel material from example 1 exposed to 10 ppm of $NO_2$.

The results are given in FIG. 1.

Experiment 3

Application in the Detection of $NO_2$

The same process as in experiment 2 is repeated for various concentrations of $NO_2$ at a flow rate of 200 ml/min. As seen previously, the slope of the variation of the absorbance, which corresponds to the rate of formation of the amylose/$I_3^-$ complex, is dependent on the concentration of $NO_2$ contained in the gas flow. Thus, the plot of the value of the slopes as a function of the concentration of $NO_2$ gives the calibration curve for the detection of $NO_2$.

Figure 2:
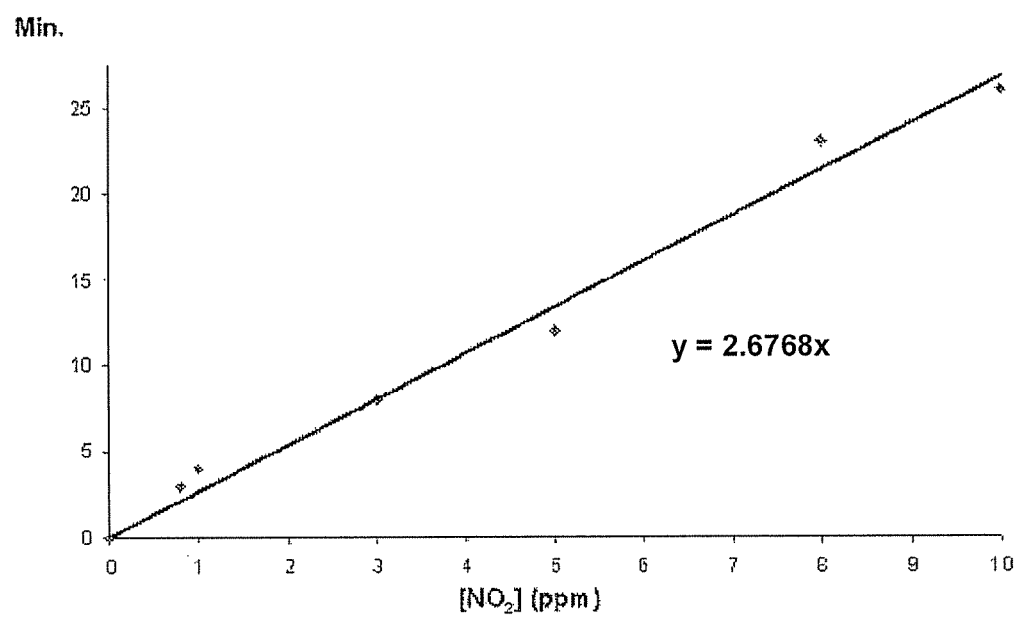
FIG. 2 represents the rate of formation of the colored complex at 580 nm as a function of the concentration of $NO_2$ contained in the studied gas, evaluated by UV-visible absorption spectroscopy of blocks of sol-gel material from example 1 exposed to $NO_2$. It is the calibration curve for the detection of $NO_2$.

The results are plotted in FIG. 2.

Experiment 4

Application in the Detection of $NCl_3$

The procedure of experiment 2 is followed. However, in this case, the gas flow studied is pretreated in order to eliminate all the chlorinated species with the exception of the trichloramine $NCl_3$. For this purpose, the gas flow passes through a filter consisting of neutral silicate matrices impregnated with sulfamic acid, in which medium only $NCl_3$ is insoluble and stable. The gas now containing only $NCl_3$ is brought into contact with the sol-gel material from example 1.

A block of sol-gel material from example 1 is then exposed to a continuous gas flow of 200 ml/min containing a fixed concentration of $NCl_3$ of 32 ppb. Monitoring by UV-visible absorption spectroscopy over the exposure time makes it possible to observe the appearance of a peak at 580 nm characteristic of the amylose/$I_3^-$ complex. The intensity of this peak increases in the course of the exposure, which means that the greater the amount of $NCl_3$, the greater the amount of colored product formed.

The results are given in FIG. 3.

For a gas flow of fixed pollutant concentration and flow rate, the slope of the variation of the absorbance at 580 nm, which corresponds to the rate of formation of the amylose/$I_3^-$ complex, is dependent on the concentration of $NCl_3$ contained in the gas flow.

Figure 4:
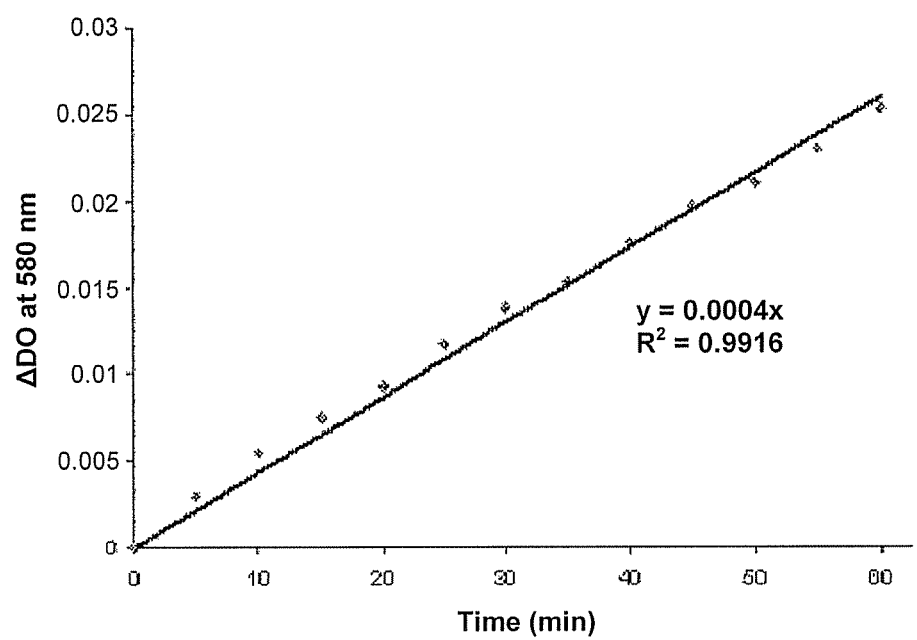
FIG. 4 represents the kinetics for formation of the complex at 580 nm for a concentration of $NCl_3$ that is fixed and equal to 32 ppb as a function of time for blocks of sol-gel material from example 1 exposed to a gas mixture containing $NCl_3$.

The results are given in FIG. 4.

Experiment 5

Application in the Detection of $NCl_3$ in Pulsed Mode

The procedure of example 4 is followed, but a same block is exposed over 2 minutes to a gas flow containing a fixed concentration of $NCl_3$ followed by a period of 5 min with no gas flow. The reaction is monitored by UV-visible absorption spectroscopy at 580 nm. This step is repeated several times. For each exposure, the variation of the absorbance at 580 nm is collected as a function of time, and the corresponding slopes are determined.

The average of the values of the various slopes (or rate of formation of the complex in $min^{-1}$, s) is taken. For a concentration of $NCl_3$=45 ppb, the average slope is 0.0017 $min^{-1}$.

The same process is repeated for various concentrations of $NCl_3$ at a flow rate of 200 ml/min. The slope of the variation of the absorbance, which corresponds to the rate of formation of the amylose/$I_3^-$ complex, is dependent on the concentration of $NCl_3$ contained in the gas flow. Thus, the plot of the average value of the slopes as a function of the concentration of $NCl_3$ gives the calibration curve for the detection of $NCl_3$.

Thus, a same sensor may be used several times, and it is possible to calculate the average of the values of the various slopes obtained in order to refine a result.

Experiment 6

Application in the Detection of HClO/ClO⁻ in Aqueous Solution

Various solutions containing various concentrations of hypochlorous acid HClO between $10^{-4}$ and $5 \times 10^{-3}$ mol/l, which have a pH=7.5, are prepared.

A drop, having a volume of around 10 µl, of each of the solutions above is deposited on blocks of sol-gel material from example 1. The droplets are left to diffuse into the porous material for 30 minutes. The diffusion of the drop leads to a color change of the initially transparent sensor, due to the reaction between the probe molecule and the chlorinated species in solution. This reaction, which results in the formation of a complex that absorbs at 580 nm, is monitored by UV-visible absorption spectroscopy.

Figure 5:
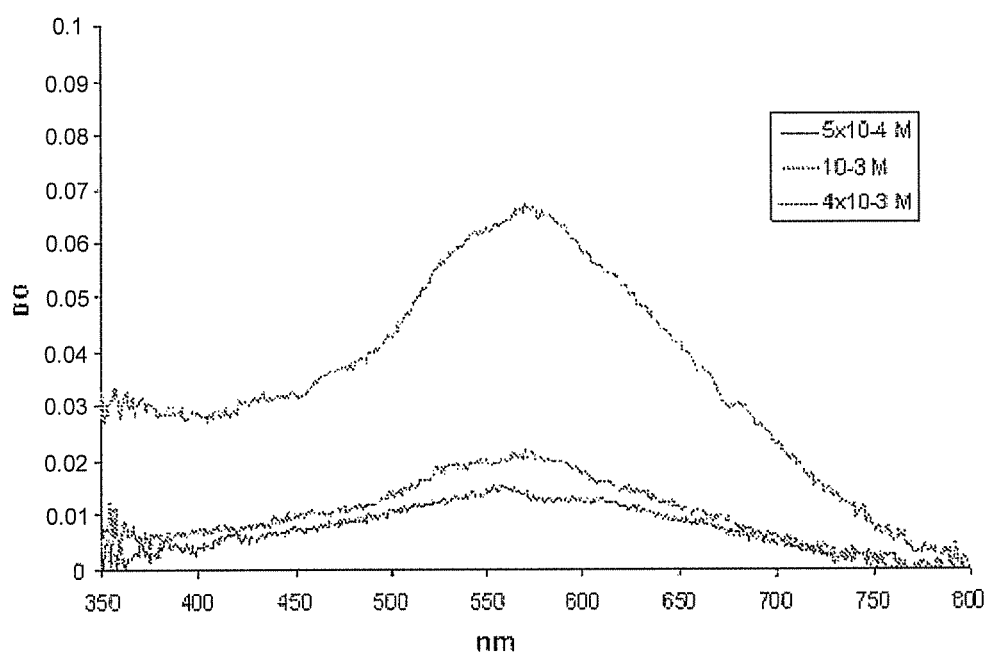
FIG. 5 represents the monitoring, by UV-visible absorption spectroscopy, of the formation of the amylose/$I_3^-$ complex for an exposure of the block of sol-gel material from example 1, over 30 min, to droplets of water containing various concentrations of HClO.
Figure 6:
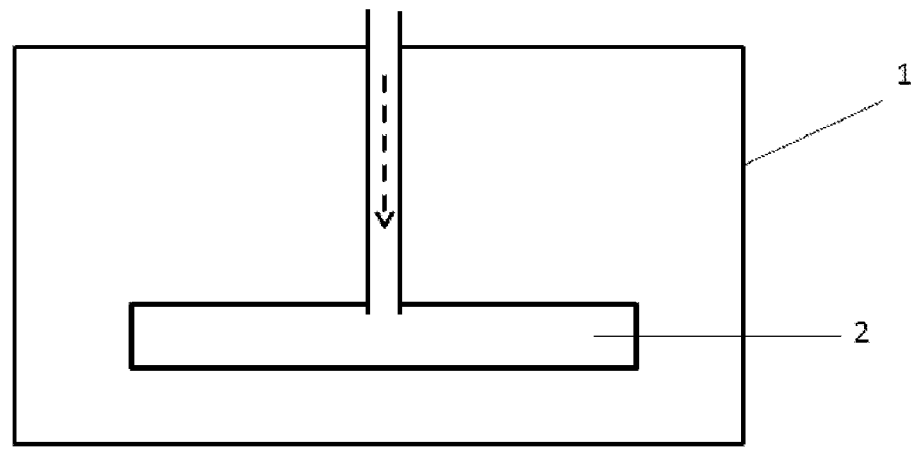
FIG. 6 is a schematic view of a multifunctional detector (1) according one embodiment disclosed herein, including a first sensor (2).

The result obtained is shown in FIG. 5.

The intensity of the peak at 580 nm is directly connected to the concentration of chlorinated species present in the solution to be analyzed.

The invention claimed is:

1. A multifunctional detector for gaseous compounds or mixtures of gaseous compounds selected from $NH_2Cl$; $NHCl_2$; $NCl_3$; total chlorine; $NO_n$, where n=1 or 2; $O_3$; and $X_2$, where X=Cl, Br or I in a sample, said detector comprising a first sensor consisting of i) a block of sol-gel material that absorbs in the UV but not in the visible ii) an iodide and iii) a reactive compound selected from starch, amylose, amylopectin, xyloglucan, xylane, chitosan, glycogen, polyvinyl alcohol or a polyvinyl alcohol compound, cellulose or a cellulose compound, α-cyclodextrin, theobromine and block polymers of polypropylene oxides and polyethylene oxides, wherein the iodide and the reactive compound are incorporated into the block of sol-gel material.

2. The multifunctional detector as claimed in claim 1, characterized in that in a block of sol-gel material of the first sensor, the iodide represents from 0.0054% to 0.55% by weight of the block.

3. The multifunctional detector as claimed in claim 1, characterized in that in a block of sol-gel material of the first sensor, the reactive compound represents from 0.05% to 0.25% by weight of the block.

4. The multifunctional detector as claimed in claim 1, suitable for gaseous compounds or mixtures of gaseous compounds selected from $NH_2Cl$; $NHCl_2$; $NCl_3$; total chlorine; $NO_n$ where n=1 or 2; $O_3$; and $X_2$ where X=Cl, Br or I in a gaseous sample, said detector further comprising a first compartment containing the first sensor; and a second compartment comprising a second sensor, wherein the second sensor comprises phenol, sodium hydroxide, and sodium nitroprussiate, incorporated into a sol-gel matrix that absorbs in the UV but not in the visible.

5. The multifunctional detector as claimed in claim 4, wherein the first compartment is sub-compartmentalized in order to contact two portions of the gaseous mixture, wherein the first portion of the gaseous mixture contacts a first sub-compartment containing a first sensor and the second portion of the gaseous mixture contacts a second sub-compartment containing a second first sensor, wherein the first portion of the gaseous mixture passes through a filter comprising a neutral silicate matrix impregnated with sulfamic acid to eliminate all the chlorinated species with the exception of $NCl_3$ before contacting the first sub-compartment of the first sensor, said filter being placed upstream of the first sensor.

6. The multifunctional detector as claimed in claim 5, wherein in the filter comprising a neutral silicate matrix, the sulfamic acid represents from 5% to 15% by weight of the total of the silicate and sulfamic acid constituents of the neutral silicate matrix.

7. The multifunctional detector as claimed in claim 5, wherein in the second sensor, the phenol represents from 10% to 25% by weight of the block of sol-gel material.

8. The multifunctional detector as claimed in claim 5, wherein in the second sensor, sodium nitroprussiate represents from 0.01% to 0.25% by weight of the block of sol-gel material.

9. The multifunctional detector as claimed in claim 5, wherein in the second sensor sodium hydroxide represents from 1% to 17% by weight of the block of sol-gel material.

10. A process for detecting gaseous compounds or a mixture of gaseous compounds selected from $NH_2Cl$; $NHCl_2$; $NCl_3$; total chlorine; $NO_n$, where n=1 or 2; $O_3$; and $X_2$ where X=Cl, Br or I contained in a liquid or gaseous sample, comprising exposing the multifunctional detector of claim 5 to a flow of a gas mixture or to a liquid and observing any color change of the blocks of sol-gel material of the first sensor or of the second sensor, and optionally identifying the presence of the gaseous compounds in the sample when a color change is observed.

11. A method for detecting of gaseous compounds or mixtures of gaseous compounds selected from $NH_2Cl$; $NHCl_2$; $NCl_3$; total chlorine; $NO_n$, where n=1 or 2; $O_3$; and $X_2$ where X=Cl, Br or I contained in a gas mixture sample, comprising contacting the multifunctional detector of claim 5 with said gas mixture sample and detecting said compounds with said detector.

12. The multifunctional detector as claimed in claim 4, wherein in the second sensor, the phenol represents from 10% to 25% by weight of the block of sol-gel material.

13. The multifunctional detector as claimed in claim 4, wherein in the second sensor, sodium nitroprussiate represents from 0.01% to 0.25% by weight of the block of sol-gel material.

14. The multifunctional detector as claimed in claim 4, wherein in the second sensor sodium hydroxide represents from 1% to 17% by weight of the block of sol-gel material.

15. A process for detecting gaseous compounds or a mixture of gaseous compounds selected from $NH_2Cl$; $NHCl_2$; $NCl_3$; total chlorine; $NO_n$, where n=1 or 2; $O_3$; and $X_2$ where X=Cl, Br or I contained in a liquid or gaseous sample, comprising exposing the multifunctional detector of claim 4 to a flow of a gas mixture or to a liquid and observing any color change of the blocks of sol-gel material of the first sensor or of the second sensor, and optionally identifying the presence of the gaseous compounds in the sample when a color change is observed.

16. A method for detecting gaseous compounds or mixtures of gaseous compounds selected from $NH_2Cl$; $NHCl_2$; $NCl_3$; total chlorine; $NO_n$, where n=1 or 2; $O_3$; and $X_2$ where X=Cl, Br or I contained in a gas mixture sample, comprising contacting the multifunctional detector of claim 4 with said gas mixture sample and detecting said compounds with said detector.

17. The multifunctional detector as claimed in claim 1, wherein the multifunctional detector further comprises a filter comprising a neutral silicate matrix impregnated with sulfamic acid in order to eliminate all the chlorinated species with the exception of $NCl_3$ from at least a portion of the gaseous compounds or mixtures of gaseous compounds before bringing into contact with the first sensor.

18. The multifunctional detector as claimed in claim 17, wherein in the filter comprising a neutral silicate matrix, the sulfamic acid represents from 5% to 15% by weight of the total of the silicate and sulfamic acid constituents of the neutral silicate matrix.

19. The multifunctional detector as claimed in claim 1, said detector further comprising two first sensors, a first compartment containing one of the two first sensors; and a second compartment containing the other of the two first sensors, wherein the first and second compartments contact two portions of the gaseous mixture, wherein the first portion of the gaseous mixture contacts the first sensor located in the first compartment and the second portion of the gaseous mixture contacts the other first sensor located in the second compartment, wherein the first portion of the gaseous mixture passes through a filter comprising a neutral silicate matrix impregnated with sulfamic acid to eliminate all the chlorinated species with the exception of $NCl_3$ before contacting the first sensor located in the first compartment, said filter being placed upstream of the first sensor.

20. A method for detecting gaseous compounds or mixtures of gaseous compounds selected from $NH_2Cl$; $NHCl_2$; $NCl_3$; total chlorine; $NO_n$, where n=1 or 2; $O_3$; and $X_2$ where X=Cl, Br or I contained in a gas mixture sample, comprising contacting the multifunctional detector of claim 1 with said gas mixture sample and detecting said compounds with said detector.

21. A process for trapping gaseous compounds selected from $NH_2Cl$; $NHCl_2$; $NCl_3$; total chlorine; $NO_n$, where n=1 or 2; $O_3$; and $X_2$ where X=Cl, Br or I contained in a gas mixture or in a liquid sample, using either the first sensor of claim 1, or
a second sensor comprising phenol, sodium hydroxide, and sodium nitroprussiate, incorporated into a sol-gel matrix that absorbs in the UV but not in the visible, wherein said process is conducted when said gas mixture or liquid sample is brought into contact with the first or second sensor, or such a flow is made to circulate over first or second sensor.

22. A system for trapping or detecting gaseous compounds contained in a gas mixture or in a liquid sample, comprising, as a sensor, the multifunctional detector of claim 1, wherein in said detector is further characterized by one or more of the features:
  (a) in a block of sol-gel material of the first sensor, the iodide represents from 0.0054% to 0.55% by weight of the block;
  (b) the reactive compound represents from 0.05% to 0.25% by weight of the block, or
  (c) the multifunctional detector further comprises a filter comprising a neutral silicate matrix impregnated with sulfamic acid in order to eliminate all the chlorinated species with the exception of $NCl_3$ from at least a portion of the gaseous compounds or mixtures of gaseous compounds before bringing into contact with the first sensor.

23. The system of claim 22, wherein said detector further comprises a second type of sensor comprising phenol incorporated in a sol-gel matrix that absorbs in the UV but not in the visible.

24. The system of claim 23, wherein in the block of sol-gel material of the second sensor, the phenol represents from 10% to 25% by weight of the block.

25. The system of claim 23, wherein in the block of sol-gel material of the second sensor, sodium nitroprussiate represents from 0.01% to 0.25% by weight of the block.

26. The system of claim 23, wherein the block of sol-gel material of the second sensor comprises sodium hydroxide which represents from 1% to 17% by weight of the block.

27. The system of claim 23, wherein in the filter comprising a neutral silicate matrix, the sulfamic acid represents from 5% to 15% by weight of the total of the silicate and sulfamic acid constituents of the neutral silicate matrix.

28. A process for detecting gaseous compounds or a mixture of gaseous compounds contained in a liquid or gaseous sample comprising:
  exposing a sample comprising gaseous compounds or mixtures of gaseous compounds selected from $NH_2Cl$; $NHCl_2$; $NCl_3$; total chlorine; $NO_n$, where n=1 or 2; $O_3$; and $X_2$ where X=Cl, Br or I to a multifunctional detector said detector comprising a first sensor consisting of i) a block of sol-gel material that absorbs in the UV but not in the visible ii) an iodide and iii) a reactive compound selected from starch, amylose, amylopectin, xyloglucan, xylane, chitosan, glycogen, polyvinyl alcohol or a polyvinyl alcohol compound, cellulose or a cellulose compound, α-cyclodextrin, theobromine and block polymers of polypropylene oxides and polyethylene oxides, wherein the iodide and the reactive compound are incorporated into the block of sol-gel material, and
  observing any color change of the block of sol-gel material constituting the first sensor.

29. A sol-gel sensor that absorbs in the UV but not in the visible produced by a process consisting of:
  (a) dissolving in an aqueous solution a reactive compound selected from starch, amylose, amylopectin, xyloglucan, xylane, chitosan, glycogen, polyvinyl alcohol or a polyvinyl alcohol compound, cellulose or a cellulose compound, α-cyclodextrin, theobromine and block polymers of polypropylene oxides and polyethylene oxides;
  (b) homogenizing the aqueous solution and reactive compound solution of (a);
  (C) boiling the homogenized solution of (b), and then cooling the boiled solution to ambient temperature
  (d) adding an alkoxide of formula $M(OR)_n$ where M is a metal and R is an alkyl group;
  (e) adding sodium iodide in solid form;
  (f) stirring the sol material from (e) in the dark and at ambient temperature; and
  (g) optionally shaping the sol material from (f) in a desired form.

30. A sol-gel sensor that absorbs in the UV but not in the visible produced by a process consisting of:
  (a) dissolving phenol, sodium nitroprussiate, and sodium hydroxide in an aqueous solution comprising water and methanol;
  (b) stirring the solution from (a);
  (c) cooling the solution and adding an alkoxide of formula M(OR), where M is a e and R is an alkyl group to form a sol material; and
  (d) optionally shaping the sol material from (c) in a desired form.

* * * * *